United States Patent [19]

Blaffert

[11] Patent Number: 5,812,630
[45] Date of Patent: Sep. 22, 1998

[54] EXAMINATION METHOD FOR THE EVALUATION OF LOCATION-DEPENDENT SPECTRA

[75] Inventor: Thomas Blaffert, Hamburg, Germany

[73] Assignee: U.S. Philips Corporation, New York, N.Y.

[21] Appl. No.: 305,116

[22] Filed: Sep. 13, 1994

[30] Foreign Application Priority Data

Sep. 15, 1993 [DE] Germany .......................... 43 31 317.5

[51] Int. Cl.$^6$ ....................................................... G01T 1/36
[52] U.S. Cl. .............................................. 378/83; 378/57
[58] Field of Search ................................. 378/53, 57, 83, 378/88

[56] References Cited

U.S. PATENT DOCUMENTS 5,467,404  11/1995  Vuylsteke et al. ...................... 382/274

FOREIGN PATENT DOCUMENTS

| 0354618A2 | 2/1990 | European Pat. Off. ........ G01N 21/31 |
| 0462658 | 12/1991 | European Pat. Off. . |
| 3827066A1 | 2/1990 | Germany ........................ G01N 21/59 |
| 4101544 | 7/1992 | Germany . |

OTHER PUBLICATIONS

Gianelli et al., "Multichannel Imaging Spectrophotometer for Direct Analysis of Mixtures on Thin–Layer Chromatography Plates", Analytical Chemistry, vol. 55, Oct. 1983, No. 12, pp. 1858–1862.

Kalivas, "Assessing Spectral Orthogonality", Applied Spectroscopy Reveiws, 25 (1989) Sep./Dec., Nos. 3/4, pp. 229–259.

W.H. Press et al, "Numerical Recipes, The Art of Scientifie Computing", pp. 52–65. No Date.

G.A. Golub et al, "Matrix Computations", 1983, pp. 16–21.

*Primary Examiner*—David P. Porta
*Assistant Examiner*—David Vernon Bruce
*Attorney, Agent, or Firm*—Anne E. Barschall

[57] ABSTRACT

The invention relates to an examination method whereby a respective spectrum with a number of spectral values is measured for a number of locations. Collective evaluation of the old spectra is enabled by the following steps:

a) formation of a data matrix from the spectral vectors formed by the series of spectral values of a respective spectrum, the spectral vectors being arranged in the columns (or in the rows) of the data matrix in a location-dependent manner, b) singular value decomposition of the data matrix in order to obtain three matrices whose product corresponds to the data matrix, the first (third) matrix consisting of spectrally dependent vectors, whereas the second matrix is a diagonal matrix and the third (first) matrix consists of location-dependent vectors, c) evaluation of at least one of the three matrices.

15 Claims, 5 Drawing Sheets

EXAMINATION METHOD FOR THE EVALUATION OF LOCATION-DEPENDENT SPECTRA

The invention relates to an examination method whereby a respective spectrum with a number of spectral values is measured for a number of locations, as well as to a device for carrying out the method.

BACKGROUND OF THE INVENTION

EP-OS 462 658 discloses a device for carrying out such a method. In the known device, which can be used for luggage inspection for the detection of given substances (explosives, drugs), the momentum transfer spectra are measured for a plurality of locations (referred to hereinafter as voxels) in the piece of luggage. Each of these spectra is individually compared with the spectra of the substances to be identified. In the case of adequate correspondence it may be assumed that the substance searched is indeed present in the piece of luggage, that is to say in the voxel for which the corresponding spectrum has been measured.

The known device, however, still exhibits a series of limitations:

a) When the substance searched is not present in at least such a high concentration in a voxel that it dominates the momentum transfer spectrum for this voxel, its presence can hardly be demonstrated. The presence of a substance to be identified, for example in the form of a foil, which is distributed among several or many voxels but occurs in only a low concentration in each voxel (which is to be considered as a square or cube having a side length of a few cm) cannot be demonstrated even when overall a comparatively large amount of this substance is present in the piece of luggage.

b) If the various substances were present in the examination zone in such a manner that each voxel, or the associated momentum transfer spectrum, were dominated by only one substance, it would be possible to determine first the substances from the momentum transfer spectra, and subsequently their spatial distribution. However, generally this condition is not satisfied, so that the spatial distribution cannot be determined.

c) The foregoing assumption would also make it possible to determine the spectrum of an unknown substance. However, because such a substance is usually distributed between a number of voxels, without being dominant in any voxel, such determination is not possible.

SUMMARY OF THE INVENTION

It is an object of the present invention to provide an examination method for the collective evaluation of spectra, i.e. a method enabling identification or determination of the spectral or spatial distribution even when the substances in the examination zone are distributed among several voxels, without being dominant in one voxel. On the basis of a method of the kind set forth, this object is achieved by taking the following steps:

a) formation of a data matrix from the spectrum vectors formed by the series of spectral values of a respective spectrum, the spectrum vectors being arranged in the columns (or the rows) of the data matrix in a location-dependent manner, b) singular value decomposition of the data matrix in order to obtain three matrices whose product corresponds to the data matrix, the first (third) matrix thereof consisting of spectrally dependent singular vectors, whereas the second matrix is a diagonal matrix and the third (first) matrix consists of location-dependent singular vectors.

c) evaluation of at least one of the three matrices.

Before the description is started, various terms used in the context of the invention will be defined. A "matrix" is to be understood to mean a rectangular field of (numerical) values which consists of rows and columns. A "diagonal matrix" is to be understood to mean a square matrix which comprises as many rows as there are columns and in which only the elements situated on the main diagonal of this matrix (the first element in the first row, the second element in the second row etc.) can haste a value other than zero. A (m×n) matrix is a matrix consisting of m rows and n columns. A transposed matrix is formed from a matrix by interchanging the rows and columns. The mathematical symbol used for a matrix will be written in capitals and in heavy print hereinafter (for example X). A transposed matrix is denoted by the raised index T (for example, $X^T$).

A "vector" is to be understood to mean a quantity which consists of a series of discrete numerical values and which can also be regarded as a one-dimensional matrix. When such a vector is identical to a row or a column of a matrix, it is also referred to hereinafter as a "row vector" or "column vector". The column vectors of the first matrix produced by the singular value decomposition and the row vectors of the third matrix produced by the singular value decomposition are also referred to as singular vectors.

Scalar multiplication of two vectors is to be understood to mean a method in which the first element of one vector is multiplied by the first element of the other vector, the second element of the one vector being multiplied by the second element of the other vector, etc., the products thus formed being added. The result of the scalar multiplication, i.e. the scalar product, is a number. When the scalar product has the value zero, the two vectors are orthogonal to one another. When, moreover, the numerical values of the vectors are such that the scalar products of each of these vectors with itself produces the value 1, but the value zero with any other vector, orthonormal vectors are concerned. When the column or row vectors of the matrix are orthonormal, a column orthonormal matrix or a row orthonormal matrix is concerned.

The invention is based on the assumption that the number of substances of different spectra occurring in the examination zone is smaller than the number of spectral values constituting a spectrum and smaller than the number of locations (voxels) in which a spectrum is determined.

Whereas the data matrix contains spectral information (for example, in the column direction) and spatial information (in the row direction), this information is distributed between the three matrices by the singular value decomposition in accordance with the invention, so that it can be readily evaluated. In this arrangement of the spectrum vectors in the data matrix the first matrix also contains spectral information in its singular vectors (column vectors), whereas the third matrix contains spatial information in its singular vectors (row vectors).

The second matrix, i.e. the diagonal matrix, contains values other than zero only along its main diagonal, i.e. the singular values resulting from the decomposition. These singular values can be subdivided into a first group and a second group, all singular values of the first group being significantly larger than the singular values of the second group. It has been found that the number of (significant)

singular values of the first group corresponds to the number of substances significantly present in the examination zone.

This information (i.e. the number of significant singular values) can be important, for example for the production of foodstuffs. Normally, only one substance is present in the examination zone, so that only one significant singular value will occur. However, the presence of a second significant singular value in the second matrix indicates the presence of a second substance in the examination zone, for example parts of a plastics tool broken during the production process.

In the ideal case the diagonal matrix contains as many matrix elements of a value other than zero in the main diagonal as there are substances (of non-negligibly small concentration) present in the examination zone. It follows therefrom that the column vectors in the first matrix and the row vectors in the third matrix, situated in the same column or row as one of the matrix elements of the value zero situated in the main diagonal of the second matrix, can be simply eliminated.

In practice, however, these values do not reach the value zero; because of additional influences such as noise occurring during the measurement, they reach a value other than zero. However, they are significantly smaller than the values caused by the components.

In order to reduce the mathematical effort required, therefore, in a further version of the invention the non-significant elements in the main diagonals of the second matrix are eliminated and hence also the vectors present in the same column of the first matrix or the same row of the third matrix. The accuracy of the calculation is not significantly influenced by this reduction, because the eliminated column or row vectors of the first or the third matrix essentially contain noise only. Therefore, if the three reduced matrices were multiplied by one another, the product would constitute a matrix which may be interpreted as a smoothed (noise-free) version of the data matrix.

In a preferred version of the invention for identification of a substance of known spectrum:

a) scalar multiplication is performed for the vector formed by the spectral components of this spectrum and the spectrally dependent singular vectors, b) the associated spectrally dependent singular vectors are weighted by the coefficient produced by the scalar multiplication and subsequently summed, c) the sum vector resulting from the summing operation is compared with the vector of the known spectrum.

This version enables identification of a substance of known spectrum, for example an explosive inside a piece of luggage, even when it is distributed so that only a small part of this substance is present in the various voxels. Therefore, this version is particularly suitable for luggage inspection. A further version is, therefore, characterized by its application for the detection of given substances during luggage inspection.

It can be demonstrated that the matrices arising from the singular value decomposition of the data matrix enable determination of the spatial distribution of substances in the examination zone when these substances and their spectra are known.

Therefore, in an embodiment of the invention for the determination of the spatial distribution of substances of known spectrum a) scalar multiplication is performed for the spectrum vectors, formed by the spectral values of these known spectra, and the spectrally dependent vectors, and b) the spatial distribution of the substances is determined while taking into account the coefficient thus obtained as well as the second matrix and the matrix consisting of the location-dependent vectors.

For the determination of the spatial distribution, therefore, it is necessary to have advance knowledge of the substances present in the examination zone or that they can be identified on the basis of their spectrum. This situation exists in the case of inspection of foodstuffs.

It also holds that the second matrix arising from the singular value decomposition enables determination of the spectrum vector of substances in the examination zone whose spatial distribution is known. Therefore, in a version of the invention for the determination of at least one of several substances whose spatial distribution within the examination zone is known, the vectors defining the spatial distribution of the individual substances are subjected to a scalar multiplication by the location-dependent vectors, the spectra of these substances being determined from the coefficients of the second matrix thus determined and from the matrix containing the spectrally dependent vectors.

A device for carrying out the examination method in accordance with the invention is characterized in that it comprises a) a measuring device for measuring a respective spectrum for a plurality of voxels, b) means for forming a data matrix from the spectrum vectors formed by the series of spectral values of a respective spectrum, the spectrum vectors being arranged in the columns (or the rows) of the data matrix in a location-dependent manner, c) means for singular value decomposition of the data matrix in order to obtain three matrices whose product corresponds to the data matrix, the first (third) matrix consisting of spectrally dependent vectors, whereas the second matrix is a diagonal matrix and the third (first) matrix consists of location-dependent vectors, d) means for evaluating at least one of the three matrices.

DESCRIPTION OF THE DRAWING FIGURES

An embodiment of the invention will be described in detail hereinafter with reference to the drawing. Therein:

DESCRIPTION OF THE PREFERRED EMBODIMENTS

Figure 1:
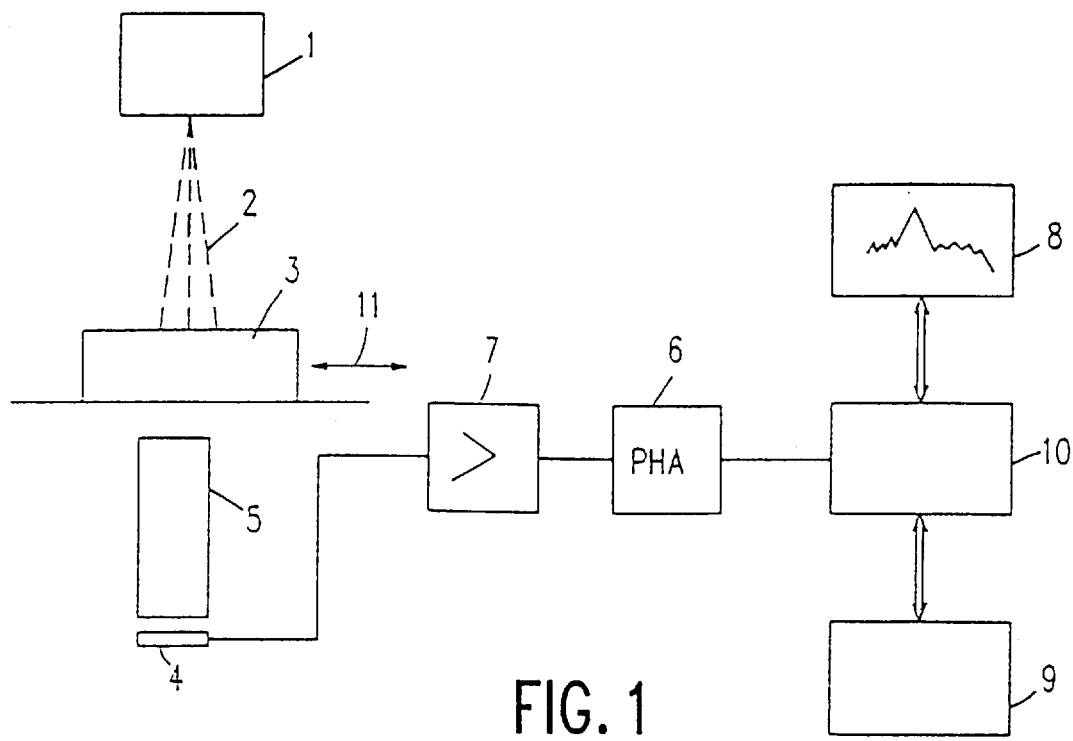
FIG. 1 shows a device for carrying out the method of the invention.

The reference numeral 1 in FIG. 1 denotes an X-ray source which emits an X-ray beam 2. The X-ray beam may be shaped as a pencil beam or as a surface of cone with a small angle of aperture. The X-ray beam irradiates an object 3 which may be a piece of luggage. However, a human body or foodstuffs can also be examined in this manner. In the object 3 the X-ray beam 2 produces inter alia elastically scattered X-rays (as is known, in the case of elastic scattering, also referred to as Rayleigh scattering, the X-ray quanta do not lose their energy after the scattering process).

The radiation beyond the object 3 to be examined is measured by means of a preferably annular detector device 4, a collimator arrangement 5 which is positioned between the object 3 and the detector 4 ensuring that the detector device 4 can mainly detect only elastically scattered X-rays at a defined scatter angle. The output signals of the detector device 4 are applied to a pulse height analyser 6 via an amplifier 7. The pulse-shaped output signals of the detector device 4 have an amplitude which is proportional to the energy of the scattered X-ray quanta and the pulse height analyser 6 generates a digital data word for each output pulse, which data word characterizes the energy of the relevant measured X-ray quantum. The signals supplied by the pulse height analyser 6 thus correspond to the energy spectrum of the X-ray quanta detected by the detector device 4 or a detector element associated therewith. Generally speaking, the detector device consists of a plurality of detector elements, each of which is struck by scattered radiation only at a given scatter angle. In this case a processing channel consisting of the components 6 and 7 is provided for each detector element.

An evaluation unit 10, which may comprise (not shown) a suitably programmed microcomputer as well as a memory 9, determines the momentum transfer spectrum from the energy spectrum, which momentum transfer spectrum can be displayed, for example on a monitor 8. The momentum transfer of an X-ray quantum is calculated in conformity with the formula $$x = \sin(\beta/2)/L \qquad (1)$$

Therein, $\beta$, is the scatter angle at which the relevant X-ray quantum is deflected by the scattering process and L is the wavelength of the scattered radiation. Because the value 1/L is proportional to the energy of the X-ray quanta measured by the pulse height analyser 6 and because the scatter angle $\beta$ of the X-ray quanta that can be detected by the detector device is predetermined by the geometry of the collimator device 5, the momentum transfer can be readily determined from the energy of the X-ray quanta or the associated wavelength L and from the predetermined scatter angle $\beta$, and the energy spectrum can be converted into a momentum transfer spectrum.

Figure 2A:
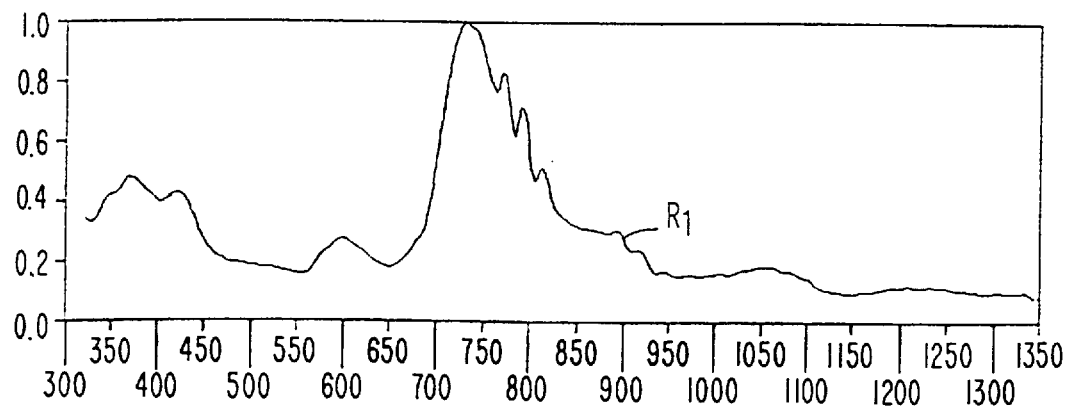
FIGS. 2a and 2b show the reference spectra of two different substances.
Figure 2B:
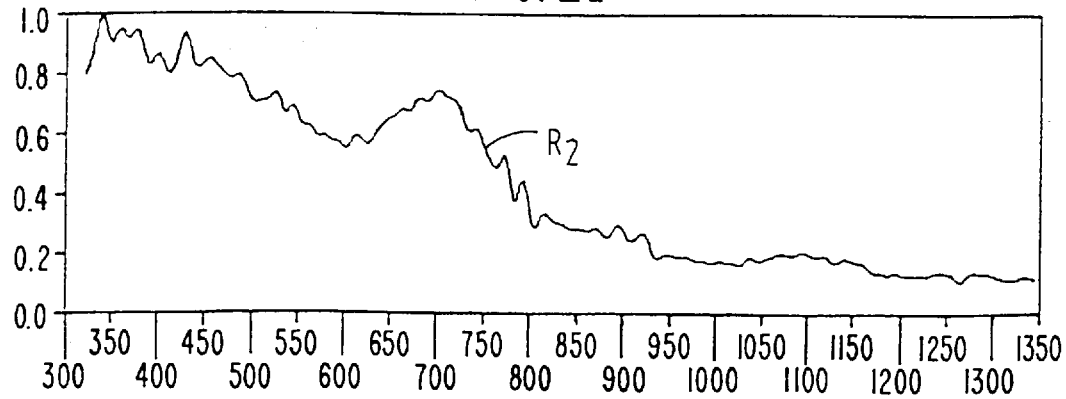

The curve $R_1$ in FIG. 2a represents the momentum transfer spectrum of an explosive (Seismoplast), whereas the curve $R_2$ in FIG. 2b represents the momentum transfer spectrum of wood. Even though the spectra (also to be referred to as reference spectra hereinafter) have in both cases been normalized to the maximum intensity value, it appears that they differ substantially from one another. These differences in the momentum transfer spectrum of different substances are the basis for the detection of given substances in the examination zone or for the determination of the spatial or spectral distribution of these substances in the examination zone.

Because the scattered radiation beam 2 covers only a small part of the examination zone (one voxel), it is necessary to displace the object 3 relative to the radiation beam 2 in two mutually perpendicular directions (horizontally as well as vertically relative to the plane of drawing), thus enabling the other voxels of the object to be examined so that their momentum transfer spectrum can be determined. The means for realizing this relative displacement are not shown in detail in FIG. 1, but are merely represented symbolically by an arrow 11.

The device described thus far is known from EP-OS 462 658 as well as from DE-OS 41 01 544. Therefore, for further details reference is made to these documents.

For demonstration purposes a rectangular container filled with five different substances (rubber, wood, fabric, soap and an explosive foil) was used as an object 3 to be examined. A two-dimensional raster of n=15×17 voxels, so 255 voxels, was scanned by displacement of the object relative to the radiation beam 2, and for each voxel the momentum transfer spectrum was determined.

Figure 3:
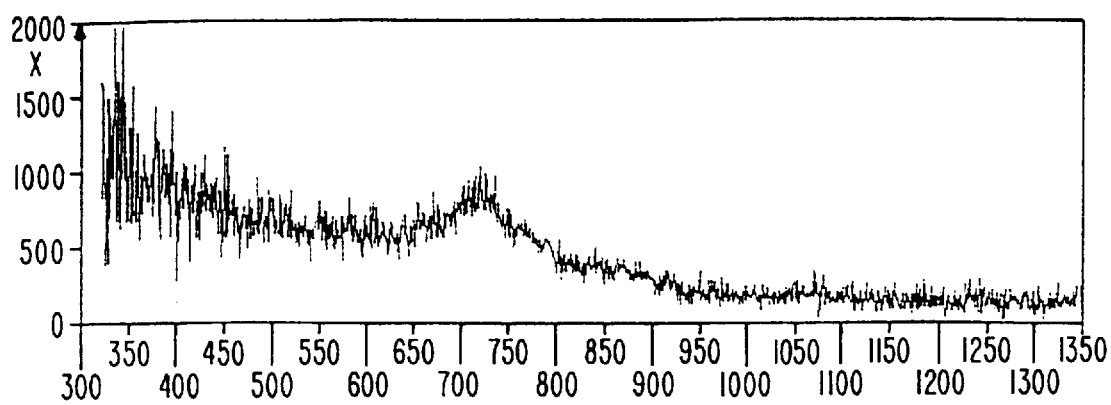
FIG. 3 shows a spectrum recorded for a single voxel.

FIG. 3 shows the momentum transfer spectrum for a voxel filled for approximately 90 vol % with wood and for approximately 10 vol % with an explosive. In comparison with the spectra shown in the FIGS. 2a and 2b, a comparatively strong noise appears. This is related to the fact that only a limited amount of time is available for the measurement of the momentum transfer spectrum for a voxel, whereas the reference spectra shown in the FIGS. 2a and 2b could be measured during a very long measurement period and hence with very low noise, because they need be measured only once after which they are stored in a library. In the spectrum shown in FIG. 3 it is virtually impossible to determine whether an explosive was present in the relevant voxel or not.

Figure 4:
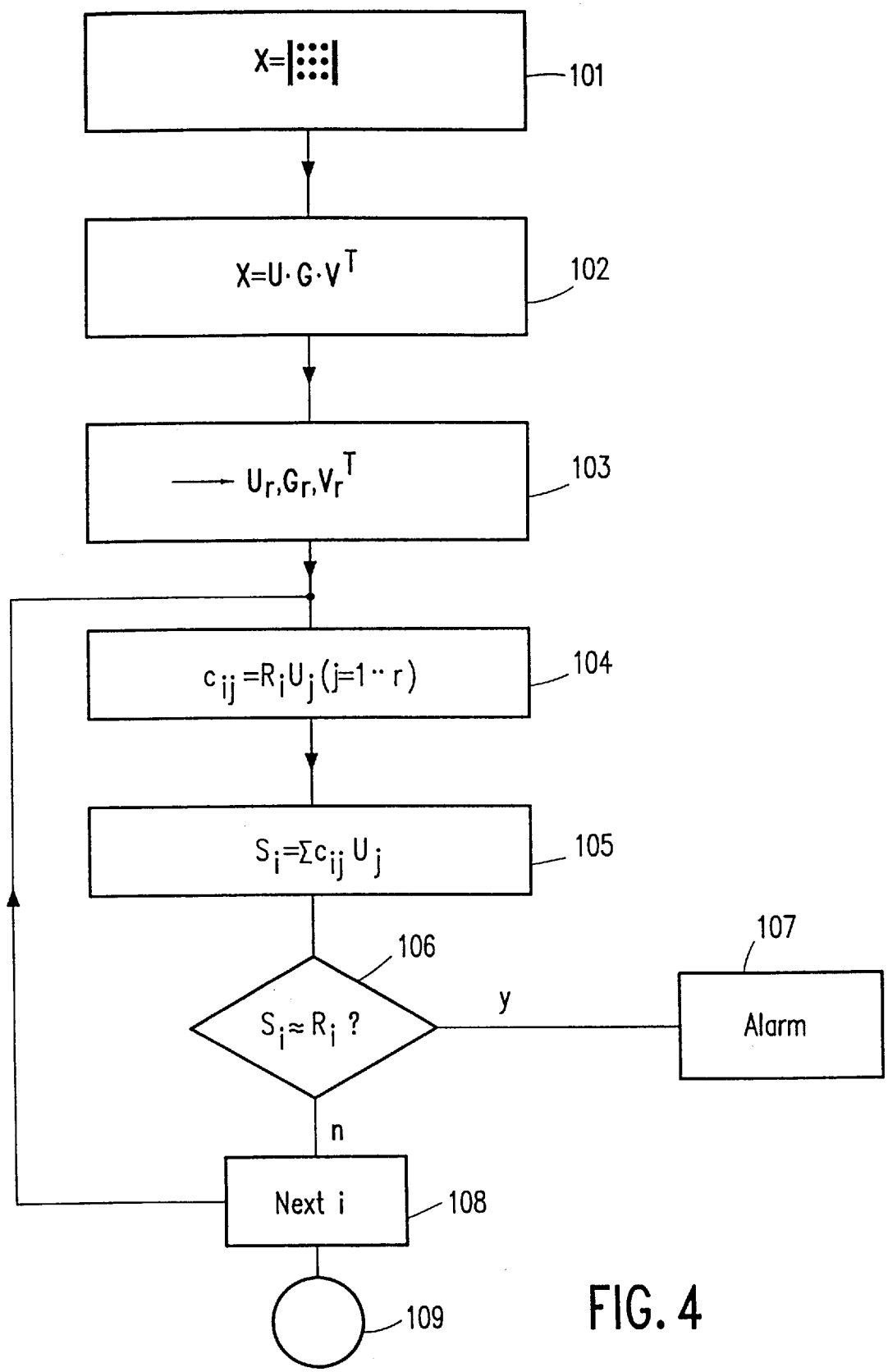
FIG. 4 shows a flow chart illustrating the method of the invention.

The method which nevertheless enables determination of whether or not an explosive is present in the examination zone defined by the n voxels will be described in detail hereinafter with reference to the flow chart of the program which is shown in FIG. 4 and which is executed by the evaluation unit 10 in processing the spectra measured.

The first step 101 consists in the formation of a data matrix. The spectrum shown in FIG. 3 is composed of m spectral values which characterize the (relative) number of X-ray quanta for a given momentum transfer; m may be, for example 1024. Because each spectrum is thus composed of a plurality of numerical values, it can be considered to be a vector in the sense of the definition given in the preamble. This vector is referred to as a "spectrum vector". For the spectrum vector of the voxel having the position i, therefore, $X_i = (x_{1i}, x_{2i}, \ldots x_{mi})$ holds. When the n spectrum vectors for the n voxels are arranged in the n columns in a data matrix X, a matrix of the following shape is obtained $$X = \begin{Vmatrix} x_{11} & \ldots & x_{1n} \\ . & & . \\ . & & . \\ . & & . \\ x_{m1} & \ldots & x_{mn} \end{Vmatrix}$$

X is, therefore, a (m×n) matrix, i.e. a matrix comprising m rows and n columns. This matrix combines location information and spectral information. Each of the rows of the matrix shows the local dependency of each time a given momentum transfer for the various voxels; each column shows the spectral dependency for a given voxel.

The next step (block 102) consists in the singular value decomposition of the data matrix into three matrices U, G, $V^T$, whose product produces the data matrix X in conformity with $$X = U \; G \; V^T \qquad (2).$$

Singular value decomposition is a known mathematical method described inter alia in a) G. H. Golub, C. F. van Loan, Matrix Computations, John Hopkins University Press, Baltimore, 1983, pp. 16–20 b) W. H. Press, B. P. Flannery, S. A. Teukolsky, W. T. Vetterling, Numerical Recipes, Cambridge University Press, 1986, pp. 52–64.

The use of this method in conjunction with spectrometry is known from DE-OS 38 27 066.

The two matrices U and $V^T$ are shaped as $$U = \begin{Vmatrix} u_{11} & \cdots & u_{1n} \\ \cdot & & \cdot \\ \cdot & & \cdot \\ \cdot & & \cdot \\ u_{m1} & \cdots & u_{mn} \end{Vmatrix} \quad \text{and} \quad V^T = \begin{Vmatrix} v_{11} & \cdots & v_{1n} \\ \cdot & & \cdot \\ \cdot & & \cdot \\ \cdot & & \cdot \\ v_{n1} & \cdots & v_{nn} \end{Vmatrix}$$

This means that the matrix U as well as the data matrix X is a (m×n) matrix, whereas the matrix $V^T$ is a square (n×n) matrix. However, this holds only for as long as the number n of voxels for which a spectrum has been measured is not larger than the number m of spectral values constituting a spectrum or a spectrum vector. If this condition is not satisfied, the matrix U is a square (m×m) matrix, whereas $V^T$ is a rectangular (n×m) matrix.

The column vectors, i.e. the singular vectors constituting the first matrix U, are orthonormal vectors, i.e. they produce the value 1 in the case of scalar multiplication by themselves and the value 0 in the case of scalar multiplication by the other column vectors. Similarly, the singular vectors of the third matrix $V^T$, i.e. its row vectors, are orthonormal vectors. U, therefore, is a column orthonormal matrix and $V^T$ is a row orthonormal matrix. When the spectrum vectors in the data matrix, form, as presumed, the column vectors, the column vectors of the first matrix contain information concerning the spectra, whereas the row vectors of the third matrix contain location-dependent information. If instead the spectrum vectors X; were arranged in the rows of the data matrix X, the column vectors of the first matrix would contain the location information and the row vectors of the third matrix would contain information concerning the spectra.

Figure 6:
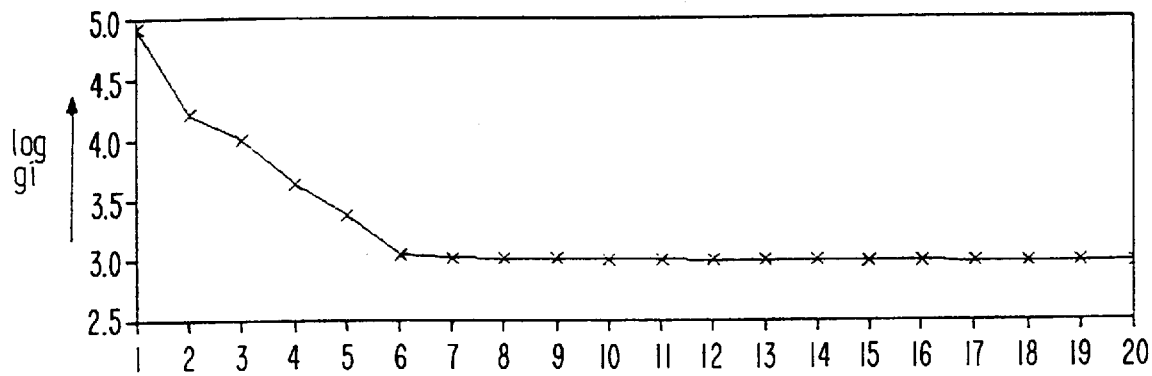
FIG. 6 shows the elements of the spectral matrix, arranged according to magnitude, at a logarithmic scale.
Figure 5A:
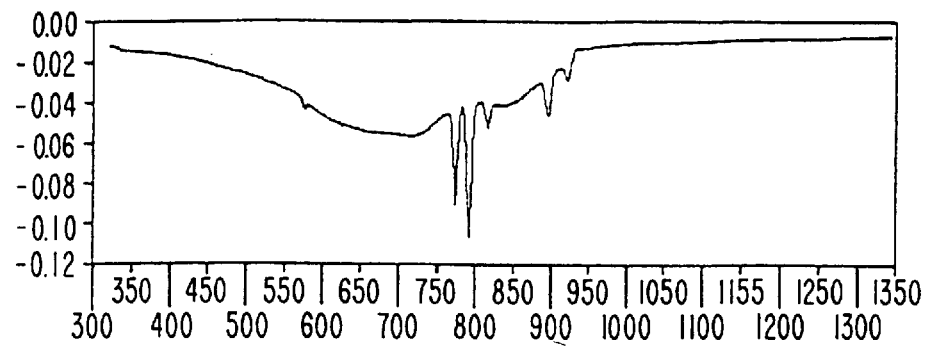
FIGS. 5a to 5f show the spectrally dependent vectors obtained by the singular value decomposition.
Figure 5B:
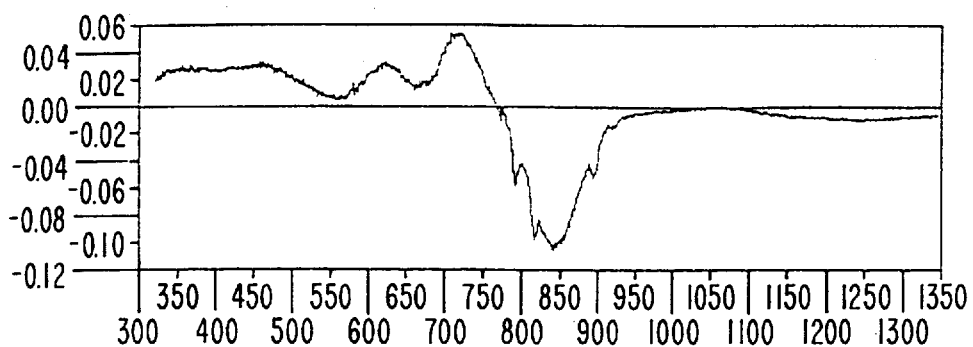
Figure 5C:
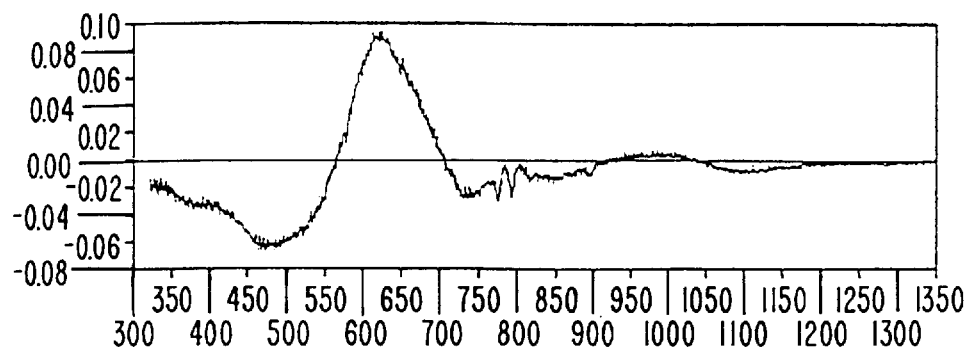
Figure 5D:
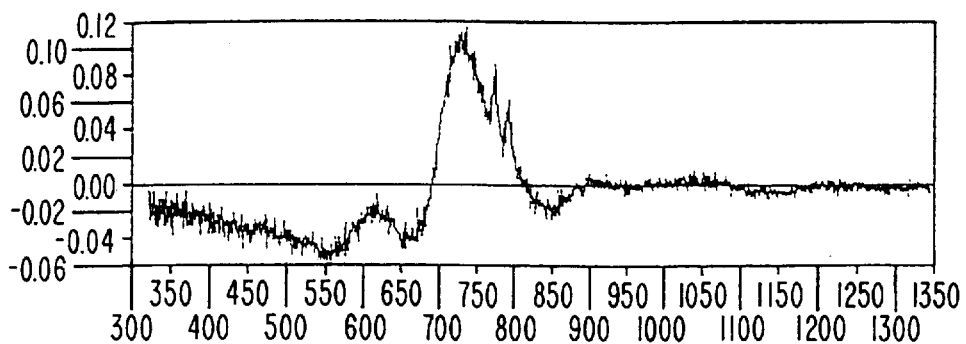
Figure 5E:
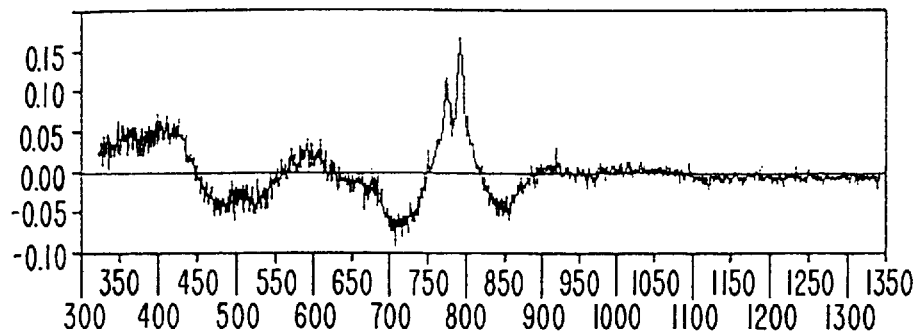
Figure 5F:
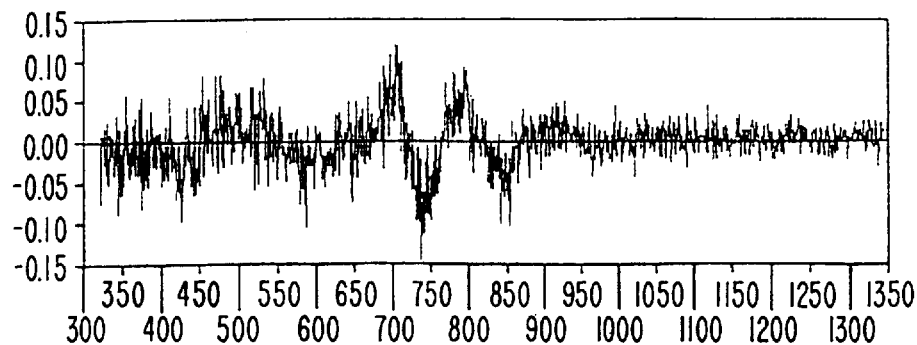

The second matrix $$G = \begin{Vmatrix} g_1 & 0 & 0 & 0 & 0 \\ 0 & g_2 & 0 & 0 & 0 \\ 0 & 0 & g_3 & 0 & 0 \\ \cdot & \cdot & \cdot & \cdot & \cdot \\ \cdot & \cdot & \cdot & \cdot & \cdot \\ \cdot & \cdot & \cdot & \cdot & \cdot \\ 0 & 0 & 0 & 0 & g_n \end{Vmatrix}$$

is a diagonal matrix in the sense of the definition given in the preamble. The matrix, elements other than zero are the singular values resulting from the singular value decomposition. They indicate the weight of the column vector of the first matrix which is situated in the same column as the relevant element, or the weight of the row vector which is situated in the same row as the associated element of the diagonal matrix. FIG. 6 shows the twenty largest singular values of the diagonal matrix G at a logarithmic scale and sorted according to magnitude. The FIGS. 5a to 5f show the column vectors of the matrix U associated with the first six singular values, i.e. the column vectors which, within the matrix U, are in the same column as the associated singular value inside, the matrix G. FIG. 5a thus shows the column vector of the matrix U associated with the largest singular value, and FIG. 5f shows the column vector associated with the sixth largest singular value.

As has already been stated, the column vectors of the first matrix U contain spectrally dependent information, i.e. each column vector represents a linear combination of the spectrum vectors of the substances present in the examination zone (which is why the spectrum vectors of the substances present in the examination zone can be reconstructed by suitable linear combinations of the column vectors). Similarly, the row vectors in the third matrix $V^T$ represent the location-dependent density distribution; for example, the second row of this matrix describes the location dependency of the density of those (abstract) components whose spectrum is formed by the second column vector of U.

The FIGS. 5a to 5f clearly show that the noise correlated with the column vectors is more pronounced as the associated singular value in the matrix G is smaller. The column vector shown in FIG. 5f, associated with the sixth largest singular value, practically no longer contains useful information but only noise. Therefore, for the examination zone in which five different substances were present there are only five column vectors with relevant spectral information.

The invention is based on the recognition of the fact that when, generally speaking, r different substances with mutually deviating spectra are present in the examination zone, the singular value decomposition produces exactly r significant matrix elements of the diagonal matrix or singular values. In ideal measuring conditions, the other singular values would be zero. In practice, however, this condition is not satisfied. The further singular values, therefore, have a value which is dependent on the noise and the other measuring errors. However, they are significantly smaller than the r first singular values as is clearly shown in FIG. 6 (for five different substances).

Therefore, it is possible, and also useful because of the reduction of the mathematical effort, to reduce the three matrices U, G and $V^T$ to the columns or rows with which a significant singular value is associated in the corresponding column or row of the diagonal matrix. This step is executed in the block 103. It means that, for example the third column vector of the matrix U and the third row vector of the matrix $V^T$ must be deleted when the singular value in the third row or column of the diagonal matrix is not significant. Furthermore, it is also useful to sort the matrices according to magnitude of the singular values, so that in the first column of the first matrix and the first row of the third matrix there are arranged the column vector and the row vector, respectively, associated with the largest singular value, provided that this sorting does not follow already from the singular value decomposition. Because of the reduction, the matrices U and V become the following matrices $U_r$ and $V_r$:

$$U_r = \begin{Vmatrix} u'_{11} & \cdots & u'_{1r} \\ \cdot & & \cdot \\ \cdot & & \cdot \\ \cdot & & \cdot \\ u'_{m1} & \cdots & u'_{mr} \end{Vmatrix} \quad \text{and} \quad V_r^T = \begin{Vmatrix} v'_{11} & \cdots & v'_{1n} \\ \cdot & & \cdot \\ \cdot & & \cdot \\ \cdot & & \cdot \\ v'_{r1} & \cdots & v'_{rn} \end{Vmatrix}$$

where $U_r$ is a (m×r) matrix and $V^T_r$ is a (r×n) matrix. The column vectors of the matrix $U_r$ are identical to a respective one of the column vectors of U, and similarly each row vector of $V^T_r$ is identical to a respective one of the row vectors. $G_r$ is a diagonal matrix of the form $$G_r = \begin{Vmatrix} g'_1 & 0 & 0 & 0 & 0 \\ 0 & g'_2 & 0 & 0 & 0 \\ 0 & 0 & g'_3 & 0 & 0 \\ . & . & . & . & . \\ . & . & . & . & . \\ . & . & . & . & . \\ 0 & 0 & 0 & 0 & g'_r \end{Vmatrix}$$

with only r singular values or r rows and columns. The singular values $g'_1 \ldots g'_r$ are the r largest values of the singular values $(g_1 \ldots g_n)$ of G. It can be demonstrated that the matrix $X_r$ resulting from the product of the three matrices $U_r$, $G_r$ and $V^T_r$ very well approximates the data matrix X and constitutes a smoothed version thereof.

The next steps, carried out in the two blocks 104 and 105, consist in that by linear combination of the column vectors still present in the matrix $U_r$, the spectrum $S_i$ is determined which represents the best possible approximation of the reference spectrum $R_i$ of the substance searched (for example an explosive having the reference spectrum $R_i$, see FIG. 2a). Because of the fact that the column vectors $U_j$ (j=1 . . . r) of the matrix are orthonormal vectors, the coefficient (or the weighting factor) with which each of the column vectors of the matrix U, describing the spectral dependency, enters the linear combination is obtained by scalar multiplication of this column vector $U_j$ (where the vector $U_j$ is composed of the components $(u_{1j}, u_{2j}, \ldots u_{mj})$) by the vector representing the reference spectrum $R_i$ of the substance searched. Thus, for the coefficient $c_{ij}$ the following equation holds:

$$c_{ij} = R_i \cdot U_j \qquad (3)$$

where "·" indicates the scalar multiplication. The calculation in conformity with the equation (3) is executed in the block 104 for all r column vectors of the matrix $U_r$.

After the calculation of the coefficient $c_{ij}$, this coefficient is used to form the linear combination $S_i$ representing the best possible approximation of the reference spectrum $R_i$ (block 105). $S_i$ is calculated in conformity with the equation $$S_i = \Sigma c_{ij} U_j$$

Summing then takes place from j=1 to j=r.

Figure 7:
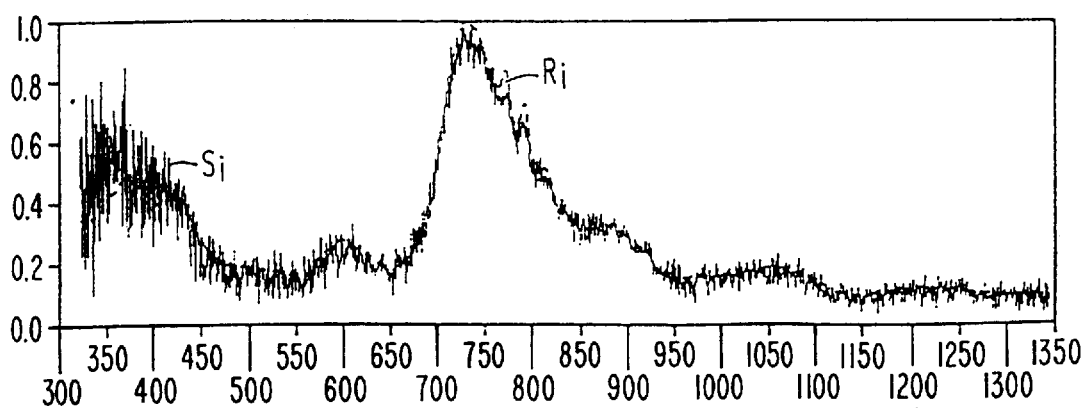
FIG. 7 shows the sum vector calculated from a linear combination of the spectrally dependent vectors in comparison with a reference spectrum.

Subsequently, a comparison is made to establish whether the sum vector $S_i$ thus formed corresponds at least approximately to the reference vector $R_i$ (block 106). FIG. 7 shows the reference vector $R_i$=R1 (for an explosive) and the sum vector $S_i$ calculated in conformity with the equations (3) and (4), the reference vector being denoted only by a dashed line. Very good correspondence is observed, which means that the substance i (explosive) has been identified in the examination zone.

The evaluation of whether $R_i$ and $S_i$ correspond at least approximately correspond can be automatically performed when for each spectral value the difference between $R_i$ and $S_i$ is formed and squared and when the squares thus calculated are added for all spectral values. The root of this sum is divided by the sum of the spectral values of the reference spectrum $R_i$ (being the area below the curve $R_i$). When the value thus formed drops below an alarm threshold value, adequate correspondence between $S_i$ and $R_i$ can be assumed, i.e. the substance searched has been found. In that case an alarm is triggered (block 107), for example an acoustic alarm or a visual alarm, the spectra $R_i$ and $S_i$ then being displayed, for example on the monitor 8 (FIG. 1).

When further substances, having a different reference spectrum, are to be detected or identified, the associated reference spectrum is loaded (step 108) and the steps 104 to 106 are repeated. Otherwise the program terminates (block 109).

The identification of individual substances within a set of vectors obtained by the singular value decomposition in some respects resembles the known mathematical regression method. The singular value decomposition, however, has a better numerical stability. It can also be executed when only the spectrum of the substance to be identified is known. The known regression methods, however, require knowledge of the spectra of all substances present in sufficient amounts in the examination zone.

A further advantage of the method of the invention consists in that it enables determination of the spatial distribution of substances when all substances present in significant amounts in the examination zone as well as their reference spectra are known. This is because the following relation holds $$C^T D = G_r \qquad (5)$$

Therein, $G_r$ is the matrix obtained after the singular value decomposition (block 102) and the reduction to the essential elements (block 103). $C^T$ is a (rxr) matrix whose row vectors are formed by the coefficients determined, in conformity with block 104, for a respective known reference spectrum $R_i$ or known substance. It is complemented in that the coefficients in conformity with the equation 104 are calculated for the known spectra $R_1$ to $R_r$ of all substances present in the examination zone. The matrix elements of the (rxr) matrix D contain information concerning the spatial distribution. They are unknown, but can be determined by solution of the equation system represented by the equation (5). After the elements of the matrix D have been determined in this manner, the density distribution can be calculated therefrom in conformity with the equation $$B = V_r D^T \qquad (6)$$

Therein, $V_r$ is the transposed of the matrix $V^T_r$ obtained by singular value decomposition and reduction to the significant components, i.e. $V_r$ can be formed from $V^T_r$ by interchanging rows and columns. $V_r$ is a (rxn) matrix (r rows, n columns). $D^T$ is the transpose of the matrix D. The matrix B resulting from the multiplication of the matrices $V_r$ and $D^T$ is also a (nxr) matrix, i.e. it consists of r column vectors with n components each. Each column vector indicates the spatial distribution among the n voxels for each time one of the r substances.

This method can be of importance for monitoring the manufacture of foodstuffs. This is because such manufacture involves few substances, for example chocolate which could be contaminated by slivers from a plastics tool used for manufacture. The reference spectra of this plastics and the chocolate can be measured and stored in advance, so that this method can be used to determine where plastics slivers can be found within the chocolate mass.

Because of the relationship between spectral information (in the matrix $C^T$) and spatial information (in the matrix D), as indicated by the equation (5), not only the spatial distribution of substances of known spectrum can be determined, but also the spectrum of substances of known spatial distribution. In this case the matrices B and $V_r$ are known in the equation (6), so that the equation system according to $D^T$ can be solved. Using the values of $D^T$ or D thus obtained, the matrix $C^T$ can be calculated by solution of the equation system indicated in equation (5); therefrom a matrix A can be calculated in conformity with the equation $$A = U_r C^T \qquad (7)$$

which matrix consists of r column vectors with m components. Each column vector represents the spectrum of one of the r substances.

I claim:

1. An examination method whereby a respective spectrum with a number of spectral values is measured for a number of locations, the method comprising the following steps:
   a) forming a data matrix (X) from spectrum vectors ($X_i$) formed by a series of spectral values of a respective spectrum, the spectrum vectors being arranged in columns or rows of the data matrix in a location-dependent manner,
   b) singular value decomposing the data matrix in order to obtain three matrices (U, C, $V^T$) whose product corresponds to the data matrix, the first or third matrix thereof including spectrally dependent singular vectors ($U_j$), whereas the second matrix is a diagonal matrix (G) and the third or first matrix includes location-dependent singular vectors,
   c) evaluation of at least one of the three matrices
   wherein, for identification of a substance of known spectrum,
      i) scalar multiplication is performed for
         a spectrum vector ($R_i$) formed by the spectral values of the known spectrum, and
         the spectrally dependent vectors ($U_j$), to form a coefficient ($c_{ij}$)
      ii) associated ones of the spectrally dependent singular vectors ($U_j$) are weighted by the coefficient ($c_{ij}$) and subsequently summed to form a sum vector, and
      iii) the sum vector is compared with the spectrum vector ($R_i$) of the known spectrum.

2. A method as claimed in claim 1, characterized in that the non-significant elements of the second matrix (G) are eliminated as well as the vectors present in the corresponding columns of the first matrix (U) and in the corresponding rows of the third matrix ($V^T$).

3. A method as claimed in claim 1, characterized in that it is used for the detection of given substances in luggage inspection.

4. An examination method whereby a respective spectrum with a number of spectral values is measured for a number of locations, the method comprising the following steps:
   a) forming a data matrix (X) from spectrum vectors ($X_i$) formed by a series of spectral values of a respective spectrum, the spectrum vectors being arranged in columns or rows of the data matrix in a location-dependent manner,
   b) singular value decomposing the data matrix in order to obtain three matrices (U, G, $V^T$) whose product corresponds to the data matrix, the first or third matrix thereof including spectrally dependent singular vectors ($U_j$), whereas the second matrix is a diagonal matrix (G) and the third or first matrix includes location-dependent singular vectors,
   c) evaluation of at least one of the three matrices;
   wherein for the determination of a spatial distribution of substances of known spectra:
      i scalar multiplication is performed for
         vectors ($R_i$) formed by spectral values of these known spectra and
         the spectrally dependent singular vectors ($U_j$), to form a coefficient ($c_{ij}$)
      ii the spatial distribution of the substances is determined while taking into account the coefficient ($c_{ij}$) as well as the second matrix and the matrix including the location-dependent singular vectors.

5. A method as claimed in claim 4, characterized in that non-significant elements of the second matrix (G) are eliminates as well as the vectors present in the corresponding columns of the first matrix (U) and in the corresponding rows of the third matrix ($V^T$).

6. An examination method whereby a respective spectrum with a number of spectral values is measured for a number of locations within an examination zone, the method comprising the following steps:
   a) forming a data matrix (X) from spectrum vectors ($X_i$) formed by a series of spectral values of a respective spectrum, the spectrum vectors being arranged in columns or rows of the data matrix in a location-dependent manner,
   b) singular value decomposing the data matrix in order to obtain three matrices (U, G, $V^T$) whose product corresponds to the data matrix, the first or third matrix thereof including spectrally dependent singular vectors ($U_j$), whereas the second matrix is a diagonal matrix (G) and the third or first matrix includes location-dependent singular vectors,
   c) evaluation of at least one of the three matrices characterized in that
      i) for determining a spectrum of at least one of several substances whose spatial distribution within the examination zone is known, vectors defining a spatial distribution of individual ones of the several substances are subjected to scalar multiplication by the location-dependent singular vectors to form a coefficient, and
      ii) the spectra of these substances are determined from the coefficient, from the second matrix, and from the matrix containing the spectrum-dependent singular vectors.

7. A method as claimed in claim 6, characterized in that non-significant elements of the second matrix (G) are eliminated as well as the vectors present in the corresponding columns of the first matrix (U) and in the corresponding rows of the third matrix ($V^T$).

8. A device for carrying out an examination method, comprising
   a) a measuring device (1, 2, 4 . . . 10) for measuring a series of spectral values of a respective spectrum for a plurality of voxels,
   b) means (10, 101) for forming a data matrix (X) from spectrum vectors ($X_i$) formed by the series of spectral values, the spectrum vectors being arranged in columns or in rows of the data matrix in a location-dependent manner,
   c) means (10, 102) for singular value decomposition of the data matrix in order to obtain three matrices (U, G, $V^T$) whose product corresponds to the data matrix, the first or third matrix including spectrally dependent vectors ($U_j$), whereas the second matrix is a diagonal matrix (G) and the third or first matrix including location-dependent vectors, d) means (10, 103 . . . 108) for evaluating at least one of the three matrices (U, G, $V^T$)

wherein, for identification of a substance of known spectrum, the device is arranged for performing the following operations
  i) scalar multiplication for
   a spectrum vector ($R_i$) formed by the spectral values of the known spectrum, and
   the spectrally dependent vectors ($U_j$), to form a coefficient ($c_{ij}$)
  ii) weighting of associated ones of the spectrally dependent singular vectors ($U_j$) by the coefficient ($c_{ij}$) and subsequently summed to form a sum vector, and
  iii) comparing the sum vector the spectrum vector ($R_i$) of the known spectrum.

9. The device of claim 8 wherein the device is part of a luggage inspection system.

10. A device for carrying out an examination method, comprising
  a) a measuring device (1, 2, 4 . . . 10) for measuring a series of spectral values of a respective spectrum for a plurality of voxels,
  b) means (10, 101) for forming a data matrix (X) from spectrum vectors ($X_i$) formed by the series of spectral values, the a spectrum vectors being arranged in the columns or in the rows of the data matrix in a location-dependent manner,
  c) means (10, 102) for singular value decomposition of the data matrix in order to obtain three matrices (U, G, $V^T$) whose product corresponds to the data matrix, the first or third matrix including spectrally dependent vectors ($U_j$), whereas the second matrix is a diagonal matrix (G) and the third or first matrix includes location-dependent vectors,
  d) means (10, 103 . . . 108) for evaluating at least one of the three matrices (U, G, $V^T$)
  wherein for determining a spatial distribution of substances of known spectra, the device is arranged to perform the following operations:
   i) scalar multiplication for
    vectors ($R_i$) formed by spectral values of these known spectra and
    the spectrally dependent singular vectors ($U_j$), too form a coefficient ($c_{ij}$,
   ii) determining the spatial distribution of the substances while taking into account the coefficient (G) as well as the second matrix and the matrix including the location-dependent singular vectors.

11. A device as claimed in claim 10, characterized in that non-significant elements of the second matrix (G) are eliminated as well as the vectors present in the corresponding columns of the first matrix (U) and in the corresponding rows of the third matrix ($V^T$).

12. The device of claim 10 wherein the device is part of a luggage inspection system.

13. A device for carrying out an examination method, comprising
  a) a measuring device (1, 2, 4 . . . 10) for measuring a series of spectral values of a respective spectrum for a plurality of voxels,
  (b) means (10, 101) for forming a data matrix (X) from spectrum vectors ($X_i$) formed by the series of spectral values, the spectrum vectors being arranged in the columns or in the rows of the data matrix in a location-dependent manner,
  c) means (10, 102) for singular value decomposition of the data matrix in order to obtain three matrices (U, G, $V^T$) whose product corresponds to the data matrix, the first or third matrix including spectrally dependent vectors ($U_j$), whereas the second matrix is a diagonal matrix (G) and the third or first matrix including location-dependent vectors,
  d) means (10, 103 . . . 108) for evaluating at least one of the three matrices (U, G, $V^T$)
  characterized in that
   i) for determining a spectrum of at least one of several substances whose spatial distribution within the examination zone is known, vectors defining a spatial distribution of individual ones of the several substances are subjected to scalar multiplication by the location-dependent singular vectors to form a coefficient, and
   ii) the spectra of these substances are determined from the coefficient, from the second matrix, and from the matrix containing the spectrum-dependent singular vectors.

14. A device as claimed in claim 13, characterized in that non-significant elements of the second matrix (G) are eliminated as well as the vectors present in the corresponding columns of the first matrix (U) and in the corresponding rows of the third, matrix ($V^T$).

15. The device of claim 13 wherein the device is part of a luggage inspection system.

* * * * *